(12) United States Patent
Liu et al.

(10) Patent No.: US 11,660,285 B2
(45) Date of Patent: May 30, 2023

(54) TRIPTOLIDE ACRYLATE, PREPARATION METHOD THEREFOR AND USE THEREOF

(71) Applicants: GUANGDONG PROVINCIAL HOSPITAL OF TCM, Guangdong (CN); THE SECOND AFFILIATED HOSPITAL OF GUANGZHOU UNIVERSITY OF CHINESE MEDICINE, Guangdong (CN); THE SECOND CLINICAL COLLEGE OF GUANGZHOU UNIVERSITY OF CHINESE MEDICINE, Guangdong (CN); GUANGDONG PROVINCIAL ACADEMY OF CHINESE MEDICAL SCIENCES, Guangdong (CN)

(72) Inventors: Bo Liu, Guangdong (CN); Xianzhang Huang, Guangdong (CN); Zhimin Yang, Guangdong (CN); Jun Li, Guangdong (CN); Quanfu Chen, Guangdong (CN); Liqiao Han, Guangdong (CN); Hualun Liang, Guangdong (CN); Yiqi Yang, Guangdong (CN); Kai Wang, Guangdong (CN); Xiaowan Wang, Guangdong (CN); Ennian Li, Guangdong (CN); Yi Wang, Guangdong (CN); Runyue Huang, Guangdong (CN); Yunshan Wu, Guangdong (CN); Xiaodong Han, Guangdong (CN); Jinlang Zhong, Guangdong (CN); Bidan Zheng, Guangdong (CN)

(73) Assignees: Guangdong Provincial Hospital of TCM, Guangdong (CN); The Second Affiliated Hospital Of Guangzhou University of Chinese Medicine, Guangdong (CN); The Second Clinical College Of Guangzhou University of Chinese Medicine, Guangdong (CN); Guangdong Provincial Academy Of Chinese Medical Sciences, Guangdong (CN)

( * ) Notice: Subject to any disclaimer, the term of this patent is extended or adjusted under 35 U.S.C. 154(b) by 0 days.

(21) Appl. No.: 17/790,049

(22) PCT Filed: Dec. 30, 2019

(86) PCT No.: PCT/CN2019/130056
§ 371 (c)(1),
(2) Date: Jun. 29, 2022

(87) PCT Pub. No.: WO2021/134272
PCT Pub. Date: Jul. 8, 2021

(65) Prior Publication Data
US 2023/0064939 A1    Mar. 2, 2023

(51) Int. Cl.
A61K 31/365    (2006.01)
A61P 35/00     (2006.01)
C07J 73/00     (2006.01)

(52) U.S. Cl.
CPC ............ A61K 31/365 (2013.01); A61P 35/00 (2018.01); C07J 73/00 (2013.01)

(58) Field of Classification Search
CPC ......... C07J 73/00; A61K 31/365; A61P 35/00
See application file for complete search history.

(56) References Cited

U.S. PATENT DOCUMENTS 6,599,499 B1    7/2003    Rosen et al.

FOREIGN PATENT DOCUMENTS

| CN | 1200714 C    | 5/2005 |
|----|--------------|--------|
| CN | 101235041 A  | 8/2008 |

(Continued)

OTHER PUBLICATIONS

Research progress on structural modification and pharmacological activity of main active components of Tripterygium wilfordii from "Chinese Pharmacy" 2016, vol. 27 (No. 4).

*Primary Examiner* — Theodore R. Howell
*Assistant Examiner* — George W Kosturko
(74) *Attorney, Agent, or Firm* — Julie K. Staple; Dinsmore & Shohl LLP

(57) ABSTRACT

Disclosed in the present invention is a new triptolide derivative as shown in formula (I). Also disclosed in the present invention are a preparation method for the compound and the medical use thereof in preparation of anti-cancer drugs. Triptolide acrylate of the present invention and a pharmaceutically acceptable salt thereof have anti-cancer activity, and after animal in-vivo experiments, can effectively inhibit tumor growth in animals. A plurality of in-vitro experiments proves that same can significantly increase the protein expression quantity of p53, promote the apoptosis of tumor cells, effectively inhibit the growth of the tumor cells, and have the effect of inhibiting metastasis of cancer cells. More importantly, the toxicity of the compound to normal cells is less than that of triptolide.

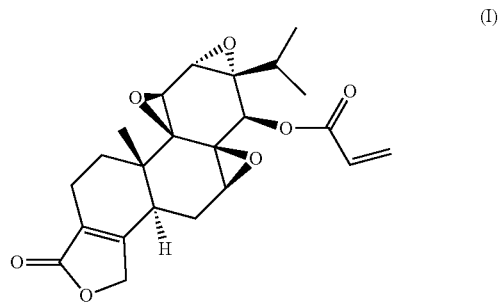

(I)

7 Claims, 6 Drawing Sheets

(56) References Cited

FOREIGN PATENT DOCUMENTS

| | | | | |
|---|---|---|---|---|
| CN | 102286065 A | 12/2011 | | |
| CN | 102786576 A | 11/2012 | | |
| CN | 104513290 A | 4/2015 | | |
| CN | 106589049 A | 4/2017 | | |
| CN | 106928312 A | 7/2017 | | |
| CN | 106946975 A | 7/2017 | | |
| CN | 108601952 A | 9/2018 | | |
| WO | WO-0012483 A1 | * 3/2000 | ........... | C07D 493/14 |
| WO | WO-0048619 A1 | * 8/2000 | ........... | A61K 31/365 |
| WO | WO-0115707 A1 | * 3/2001 | ........... | A61K 31/335 |
| WO | WO-02074759 A1 | * 9/2002 | ........... | A61K 31/365 |
| WO | WO-2008087202 A1 | * 7/2008 | ........... | A61K 31/365 |
| WO | 2016181312 A1 | 11/2016 | | |
| WO | WO-2018210224 A1 | * 11/2018 | ........... | A61K 31/573 |

* cited by examiner

TRIPTOLIDE ACRYLATE, PREPARATION METHOD THEREFOR AND USE THEREOF

CROSS-REFERENCE TO RELATED APPLICATIONS

This application is the U.S. National Stage of PCT/CN2019/130056 filed on Dec. 30, 2019, the entire content of which is incorporated herein by reference in its entirety.

FIELD OF THE INVENTION

The present invention belongs to the technical field of medicine, and in particular relates to a triptolide derivative, a preparation method therefor and medical use thereof.

BACKGROUND OF THE INVENTION

Triptolide is also known as wilforlide and triplolide. The triptolide is an epoxy diterpene lactone compound extracted from the roots, leaves, flowers and fruits of Tripterygium wilfordii. The triptolide and other alkaloids such as trypterygine, wilforine, wilforgine, wilfortrine, wilforzine and wilfordine constitute the main active components of the extract of Tripterygium wilfordii. The triptolide is insoluble in water, and is easily soluble in methanol, dimethyl sulfoxide, anhydrous ethanol, ethyl acetate, chloroform, etc. The current researches have shown that the triptolide has antioxidation, anti-rheumatoid, anti-senile dementia and anticancer effects. The modern researches have shown that the triptolide not only has an anti-rheumatoid effect, but also has anti-senile dementia and anti-cancer effects.

However, although the triptolide has better activity, the triptolide also has stronger toxicity. Clinical tests have shown that the triptolide has strong toxic and side effects on the digestive system, the urinary system, the cardiovascular system, the blood system, the allergic reaction, the nervous system, the reproductive system, etc. On the basis of ensuring a certain activity, reducing the toxicity of the triptolide is an important direction in the research of triptolide derivatives. Some research has shown that the toxicity of the triptolide is related to 12-site and 13-site epoxy rings thereof, and this group is very easy to react with a variety of proteins, resulting in a variety of biological effects.

SUMMARY OF THE INVENTION

An objective of the present invention is to provide a triptolide derivative so as to solve at least one of the above technical problems. Further, the present invention also provides a preparation method for the above compound and medical use thereof.

Another objective of the present invention is to provide a preparation method for a triptolide derivative so as to solve at least one of the above technical problems.

The triptolide derivative provided by the present invention is specifically triptolide acrylate or a pharmaceutically acceptable salt thereof, and the structural formula is shown in formula I.

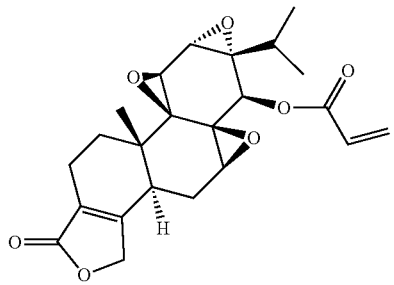

(I)

A synthetic route of the triptolide acrylate of the present invention includes:

adding triptolide and an acylating reagent (acryloyl chloride, acryloyl bromide, acrylic anhydride, acrylic acid or equivalent 3-chloropropionyl chloride thereof) to an organic solvent (anhydrous dichloromethane, trichloromethane, tetrahydrofuran or diethyl ether), using organic alkalis such as triethylamine, trimethylamine, pyridine, diisopropylethylamine (DITEA), 1,8-diazabicycloundec-7-ene (DBU), 2,6-dimethyl pyridine and 4-dimethylaminopyridine (DMAP) as acid binding agents, using 4-dimethylaminopyridine, dicyclohexylcarbodiimide (DCC), 1-hydroxy-7-azabenzotriazole (HOAT), 1-hydroxybenzotriazole (HOBT), O-benzotriazole-tetramethylurea hexafluorophosphate (HBTU), O-benzotriazole-N,N,N',N'-tetramethylurea tetrafluoroboric acid (TBTU), etc. as catalysts, performing stirring for 1-4 h (specifically can be 2 h) at a room temperature, quenching the reaction with a saturated aqueous sodium bicarbonate solution, performing extraction with dichloromethane (or other organic polar solvents having poor compatibility with water), extracting an aqueous layer with dichloromethane (or other organic polar solvents having poor compatibility with water) twice, mixing the extracts of dichloromethane (or other organic polar solvents having poor compatibility with water), washing out most of the water in the extract with a saturated aqueous sodium chloride solution, then performing drying with a desiccant (one or more water absorbing agents such as anhydrous sodium sulfate, anhydrous magnesium sulfate and anhydrous calcium chloride), performing evaporation to dryness under reduced pressure, and performing purification by silica gel column chromatography to obtain the compound shown in formula I.

The triptolide acrylate of the present invention and the pharmaceutically acceptable salt thereof have anti-cancer activity, and after animal in-vivo experiments, can effectively inhibit tumor growth in animals. A plurality of in-vitro experiments proved that same can significantly increase the protein expression quantity of p53, promote the apoptosis of tumor cells, effectively inhibit the growth of the tumor cells, and have the effect of inhibiting metastasis of cancer cells. More importantly, the toxicity of the compound to normal cells is less than that of triptolide.

In the present invention, a functional group with specific selectivity is introduced on the C14-hydroxyl group of the triptolide, and this functional group will preferentially bind to the target protein, thereby improving the selectivity and reducing the toxicity. Furthermore, since the introduced functional group is a rotatable flexible group with a moderate size, the functional group will have a certain steric effect on 12-site and 13-site epoxy rings, which can also improve the selectivity and reduce the toxicity.

DETAILED DESCRIPTION OF THE INVENTION

The present invention will be further described in detail below with reference to specific examples and accompanying drawings.

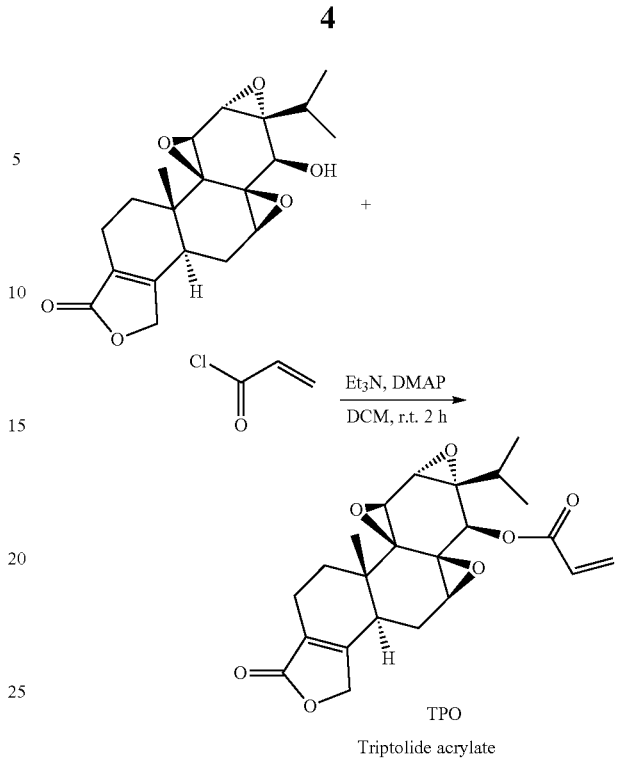

Triptolide acrylate 103.4 mg (0.287 mmol) of triptolide and 1.75 mg (0.01435 mmol) of 4-dimethylaminopyridine were taken and dissolved in 5 mL of anhydrous dichloromethane, 319.5 mg (3.157 mmol) of triethylamine was added, an ice bath was performed to about 0° C., 259.7 mg (2.87 mmol) of acryloyl chloride was dropwise added, the temperature was gradually returned to a room temperature after dropwise adding, stirring was performed to react for 2 h, TLC was performed to detect whether the reaction is complete, the stirring was stopped, the reaction was quenched with a saturated aqueous sodium bicarbonate solution, extraction was performed with dichloromethane, an aqueous layer was extracted with dichloromethane twice, dichloromethane extracts were mixed, most of the water in the dichloromethane extract was washed out with a saturated aqueous sodium chloride solution, drying was performed with anhydrous sodium sulfate, evaporation to dryness was performed under reduced pressure, separation was performed by preparing a thin-layer silica gel plate, and petroleum ether-ethyl acetate (2:1-1:1) was used as a developing solvent to obtain 32.1 mg of colorless and transparent oil of which the yield was about 27.0%. After detection, the structural formula of the compound is shown in formula I, namely triptolide acrylate.

Figure 1:
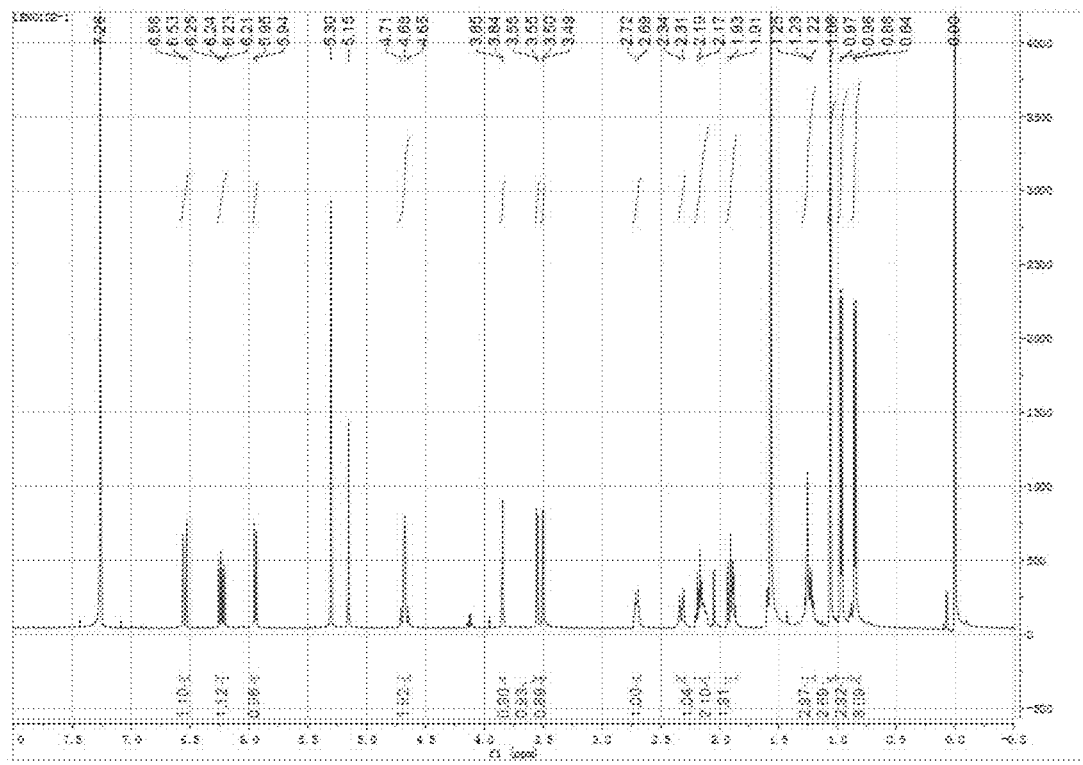
FIG. 1 shows a $^1$H NMR spectrum of triptolide acrylate.
Figure 2:
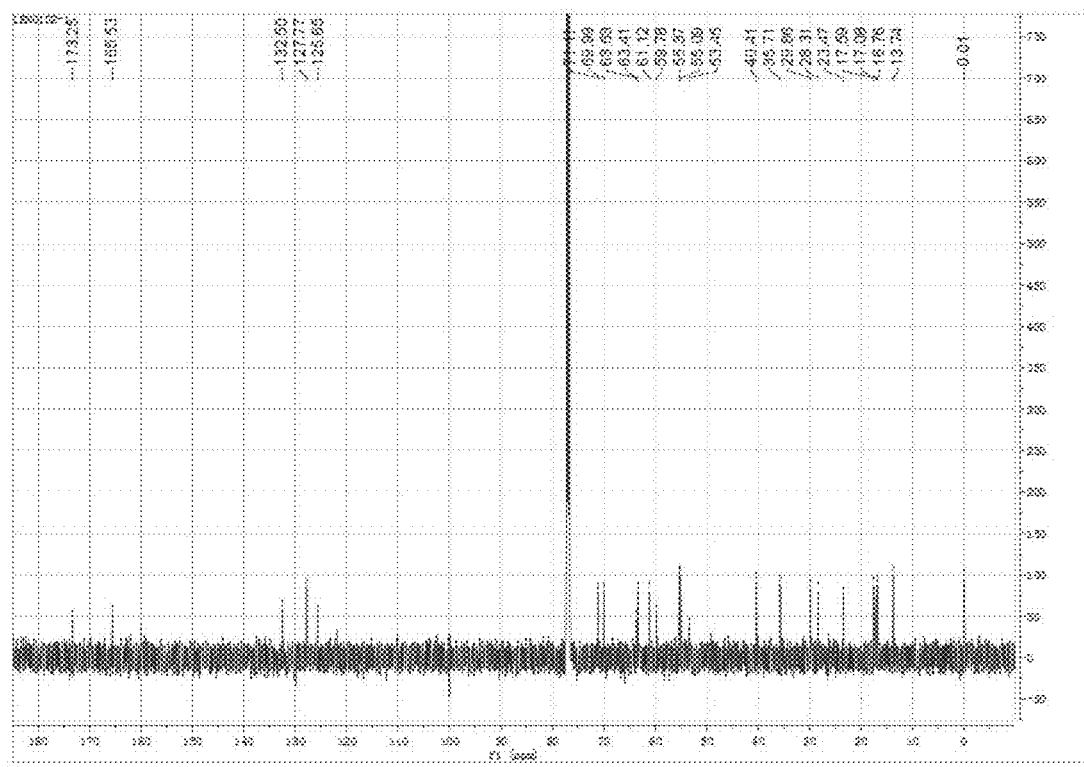
FIG. 2 shows a $^{13}$C NMR spectrum of triptolide acrylate.
Figure 3:
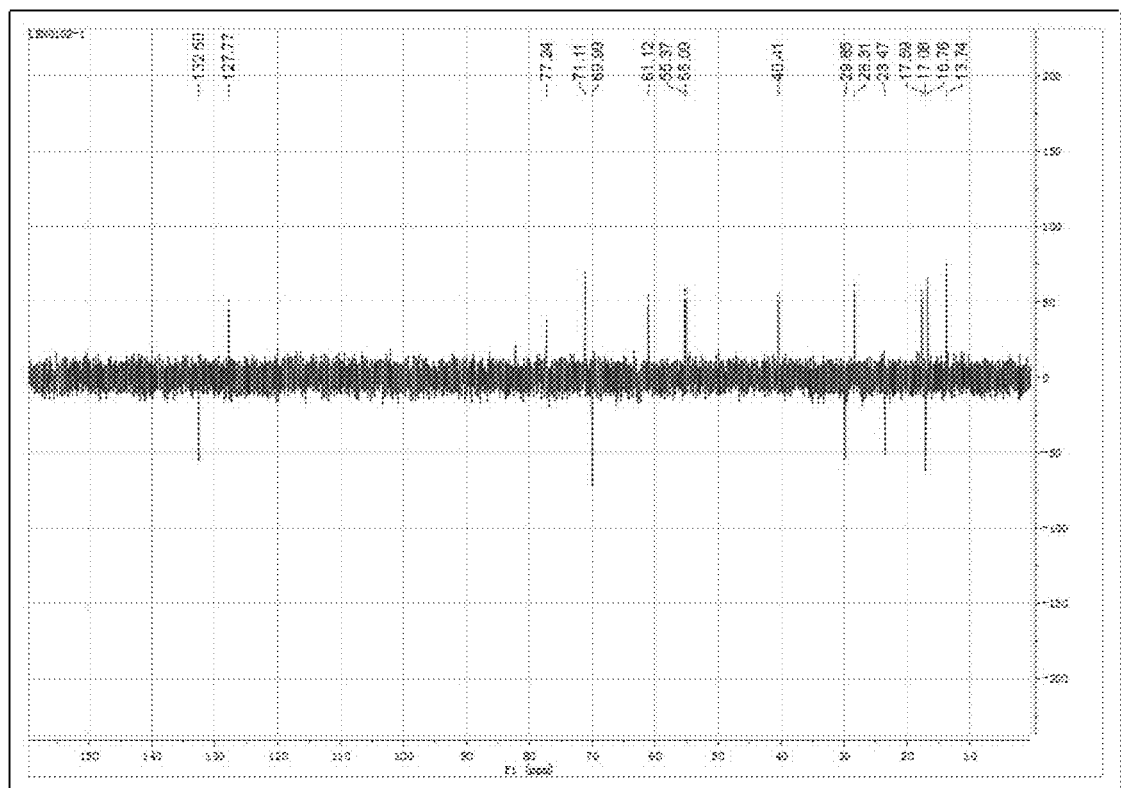
FIG. 3 shows a DEPT135 spectrum of triptolide acrylate.

As shown in FIG. 1 to FIG. 3, the molecular formula of the compound shown in formula I is $C_{23}H_{26}O_7$, and ESI-MS m/z is 414.1679 [M+H]$^+$ (theoretical value). $^1$H NMR (600 MHz, CDCl3) δ 6.54 (d, J=16.1 Hz, 1H), 6.23 (dd, J=17.3, 10.4 Hz, 1H), 5.94 (d, J=10.4 Hz, 1H), 5.15 (s, 1H), 4.77-4.61 (m, 2H), 3.84 (d, J=3.2 Hz, 1H), 3.52 (dd, J=30.8, 4.2 Hz, 2H), 2.70 (d, J=13.3 Hz, 1H), 2.32 (d, J=18.3 Hz, 1H), 2.18 (d, J=26.5 Hz, 2H), 1.90 (d, J=39.2 Hz, 2H), 1.59 (dd, J=4.8, 16.0 Hz, 1H), 1.24 (m, 1H), 1.06 (s, 3H), 0.97 (d, J=7.0 Hz, 3H), 0.85 (d, J=6.9 Hz, 3H).
$^{13}$C NMR (151 MHz, CDCl3) δ 173.24, 165.52, 159.98, 132.46 (CH$_2$), 127.78, 125.63, 71.13, 69.98 (CH$_2$), 63.64, 63.40, 61.11, 59.78, 55.36, 55.09, 40.40, 35.71, 29.86 (CH$_2$), 28.33, 23.47 (CH$_2$), 17.58, 17.08 (CH$_2$), 16.76, 13.74.

I. Inhibition experiment of triptolide acrylate on HepG2 subcutaneous implanted tumor in nude mice 1. Experimental Materials 1.1 Experimental animals: nude mice, male, 4-6 weeks, weighing about 18-20 g. The mice were purchased from Beijing Vital River Laboratory Animal Technology Co., Ltd. (certificate number: 11400700270675).

1.2 Cell: HepG2 cell line; drug: triptolide acrylate synthesized in the above example.

1.3 Other Experimental Reagents and Consumables:

sterile normal saline, surgical scissors, tweezers, vernier calipers capable of displaying readings (Guangzhou Whiga Technology Co., Ltd.), 1 mL syringe, cotton swabs; RPMI-1640 medium, DMEM medium (Gbico, USA); fetal bovine serum (Gibco, North America); penicillin-streptomycin (double antibody), 0.25% trypsin (containing EDTA); cell apoptosis kit, cell cycle kit (MultiSciences (Lianke) Biotech Co., Ltd.); cell culture flask, cell culture dish (Coring, N.Y., USA); 2 mL cryovial (Coring, Los Angeles, USA); 96-well cell culture plate, 6-well cell culture plate (Coring, Los Angeles, USA); RIPA lysate (strong), PMSF protease inhibitor, phosphatase protein compound inhibitor (Guangzhou Dingguo Biotechnology Co., Ltd.); Tween 20 (ST825, Beyotime, Guangzhou Whiga Technology Co., Ltd.), SDS-PAGE gel kit (Beyotime, Guangzhou Whiga Technology Co., Ltd.), 5× Loading Buffer (Beyotime, Guangzhou Whiga Technology Co., Ltd.); Prism Protein Marker (Thermo, USA); ECL chemiluminescent liquid (P0018A, Beyotime, Guangzhou Whiga Technology Co., Ltd.); PVDF membrane (Beyotime, Guangzhou Whiga Technology Co., Ltd.); thin filter paper, sponge, 1.5 m sheet (Bio-Rad, USA); methanol (Sinopharm Chemical Reagent Co., Ltd.); glycine (Qingdao Sangon Biotechnology Co., Ltd.), SDS (Beijing BioDee Biotechnology Co., Ltd.), Tris Base (Shanghai Baiyan Biotechnology Co., Ltd.), TBS powder (Beyotime, Guangzhou Whiga Technology Co., Ltd.); skimmed milk powder (BD, UK).

1.4 Experimental Instruments $1/10,000$ balance (Beijing Raidolis Scientific Instrument Co., Ltd.), carbon dioxide incubator (Shanghai Boxun Industrial Co., Ltd.); cell ultra-clean workbench (Esco Micro Pte. Ltd., Singapore); low-speed desk centrifuge (DT5-3, Beijing Times Beili Centrifuge Co., Ltd.); microplate reader VICTORX5 (Perkinelmer, USA); liquid nitrogen tank (Locator PLUS, USA); multifunctional refrigerated centrifuge (5430R, eppendorf, China Eppendorf Co., Ltd.), electrophoresis and membrane transfer device (Bio-Rad, USA), velocity-modulated oscillator (HS260, IKA Shanghai Shengke Instrument Equipment Co., Ltd.), thermostatic metal bath (Q872), gel imaging system (XR+) (Bio-Rad, Shanghai Laboratories Co., Ltd.), shaker (SK-L330-Pro).

2. Experimental Process 2.1 Establishment of Animal Models

Establishment of HepG2-Luc cell line stably expressing luciferase: HepG2 cells in the logarithmic growth phase were taken and placed into a 24-well plate at $1\times10^5$/well, and cultured overnight to make the cells fully adherent. An original medium was replaced with 2 mL of fresh medium containing 6 μg/mL polybrene, about $1\times10^5$ transfection units of recombinant lentiviral particles stably expressing luciferase were added, and after incubation was performed for 4 h at 37° C., 2 mL of fresh medium was added to dilute the polybrene. The culture was continued, and a virus-containing medium was replaced with a fresh medium. The culture was continued, a medium containing puromycin was replaced for resistance screening, drug-resistant clones were picked and screened for two weeks, and finally, a cell line HepG2-Luc stably expressing luciferase was obtained.

Construction of bear mice by HepG2-Luc cell line: the cryopreserved HepG2-Luc cells were recovered to a 100 $cm^2$ culture flask, cultured in vitro to the logarithmic growth phase and digested with 0.25% trypsin containing EDTA, the cells were collected and centrifuged at 1000 rpm for 3 min at a room temperature, the supernatant was discarded, the cells were washed with a serum-free DMEM medium, and the cell viability was detected by a trypan blue exclusion assay (only if the proportion of viable cells exceeded 95%, the experimental requirements were met). A small amount of the serum-free DMEM medium was added to resuspend the cells, and the cells were counted. The back skin of the nude mice was sterilized with 75% alcohol, about 200 μL of cell suspension containing $1\times10^7$ cells was inoculated into the right anterior axilla of the nude mice, and the mice were kept for a week under aseptic conditions to observe whether there were subcutaneous implanted tumors visible to the naked eye.

Detection of tumor growth by animal in-vivo imaging system: each nude mouse was intraperitoneally injected with 150 μL of 30 mg/kg fluorescein substrate and observed for 15 min, the nude mouse was anesthetized with diethyl ether in an induction box for 5 min, the anesthetized nude mouse was quickly transferred into an observation box, the head of the nude mouse was aligned and fixed in a conical nasal plug, parameters were set for fluorescence imaging (if there was tumor growth, fluorescence signals with different intensities can be detected at the corresponding positions), after the imaging, the nude mouse was transferred into the induction box again, and an oxygen valve was turned on to revive the nude mouse.

2.2 Animal Grouping and Administration

Grouping: subcutaneous tumors were observed in all nude mice after 1 week, and the growth of tumor pairs was verified by an animal in-vivo imaging technology, therefore, the nude mice were sorted and numbered according to the body weight. 18 random numbers were generated by Excel software, the random numbers were corresponding to the numbers of the nude mice, and the nude mice were equally divided into model groups according to the size of the random numbers, namely a low-dose group (100 μg/kg), a middle-dose group (200 μg/kg) and a high-dose group (400 μg/kg). After random grouping, the nude mice were weighed and the tumor volume was measured. Statistical tests were used to test the differences in body weight and tumor volume of the nude mice among the groups. If there is no difference among the groups, the balance is better, indicating that the grouping is correct.

Administration: the nude mice were administered by intraperitoneal injection, and a disposable sterile syringe was used for intraperitoneal injection of a triptolide acrylate solution. The nude mice in the model group were fed with normal saline, and the nude mice in the administration group were fed with the triptolide acrylate solution according to the dose. The nude mice were administrated once a day for 13 consecutive days.

2.3 Observation and Recording

The nude mice were routinely observed every day after administration, including mental state, activity, diet, skin color, feces, etc., the body weight of the nude mice was measured and recorded twice a week, the size of the implanted tumor was measured, and in-vivo imaging was performed once a week to monitor tumor growth and distant metastasis for 3 consecutive weeks until the end of administration.

2.4 Material Acquisition

After the administration, the animals were anesthetized, the cervical vertebrae were severed and sacrificed, the tumor was completely removed, and the size of the tumor tissue was measured and recorded.

2.5 Western Blot

After the tumor tissue was thawed on ice, 50 mg of tumor tissue was taken into a tissue homogenization tube, and 500 μL of tissue lysate containing protease inhibitors and phosphatase inhibitors was added (usage of Roche brand tablets: 1 tablet/10 mL). After high-speed homogenization, centrifugation was performed at 12,000 rpm/min for 15 min, the supernatant was taken, and the protein concentration of the sample was measured by a BCA method. After the concentration of each sample was adjusted to the same, a protein loading buffer (5× Loading buffer) was added, denaturation was performed at 100° C. for 10 min, and preservation was performed at −80° C.

An appropriate brand of 10% pre-mixed polyacrylamide gel preparation solution was selected, and then, the gel (including separating gel and stacking gel) used in the experiment was prepared according to the instructions for use, which takes about 2 h. In the process of waiting for gel solidification, an SDS-PAGE gel electrophoresis solution was prepared in advance, the prepared gel was put in an electrophoresis tank, then the electrophoresis solution was added, and 10-30 μL of sample was added to each well of loading slot. After the sample runs through the stacking gel at a low pressure of 80 V, the voltage was adjusted to 100 V to make the sample run through the entire block of gel, so as to complete the SDS-PAGE gel electrophoresis operation. Secondly, a membrane transfer operation was performed (a PVDF membrane was pre-wetted in methanol for 5 min in advance), and membrane transfer conditions were: 300 mA, 120-150 min (corresponding to the time selection of the dividing line with a molecular weight of 100 kDa, wherein the selected membrane transfer time of the separated protein with a molecular weight less than 100 kDa was 120 min, and the selected membrane transfer time of the separated protein with a molecular weight greater than 100 kDa was 150 min). After membrane transfer, 5% skimmed milk was used for sealing for 2 h, and the primary antibody was incubated overnight in a refrigerator at 4° C. according to the corresponding band. On the next day, the unbound primary antibody was washed (5 times, 5 min each time) with a TBST washing solution. The secondary antibody was incubated at 37° C. for 2 h, and the unbound secondary antibody was washed with the TBST washing solution (5 times, 5 min each time). An ECL luminescent solution was used as a substrate to expose the target band, and the results were analyzed, recorded and counted.

3. Results and Analysis 3.1 In this experiment, a liver cancer cell line HepG2-Luc that can stably express luciferase was established, and a subcutaneous liver cancer implanted tumor model of nude mice was constructed by using these cells.

Figure 4:
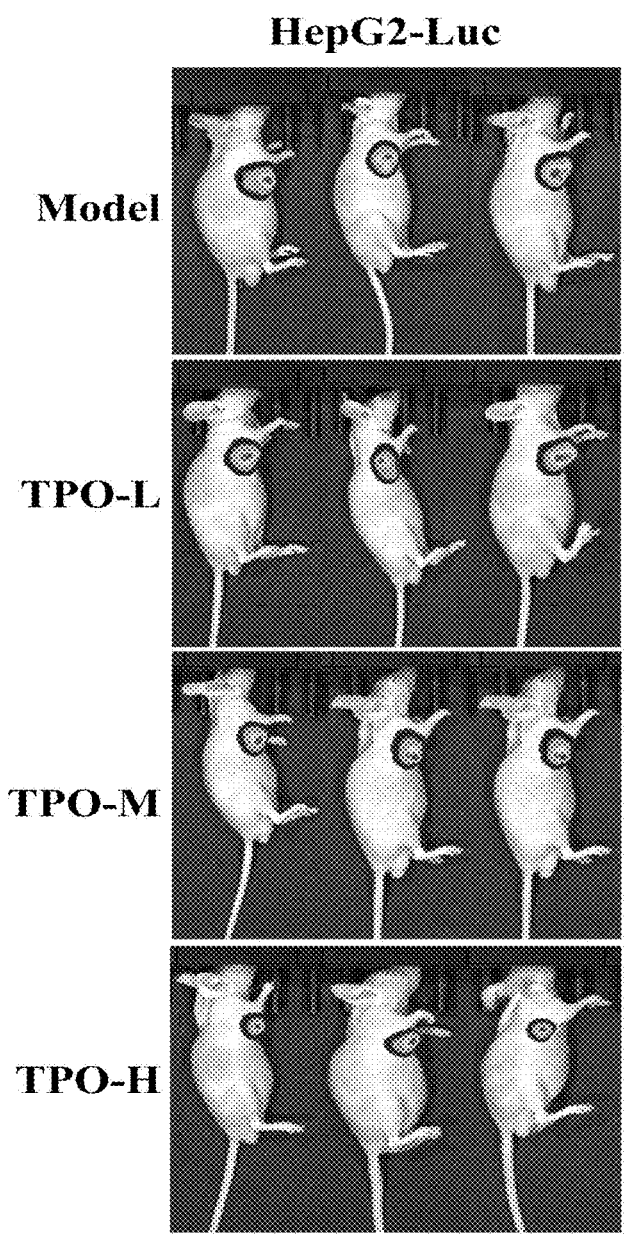
FIG. 4 shows graphs of fluorescence signals in tumors of nude mice.
Figure 5:
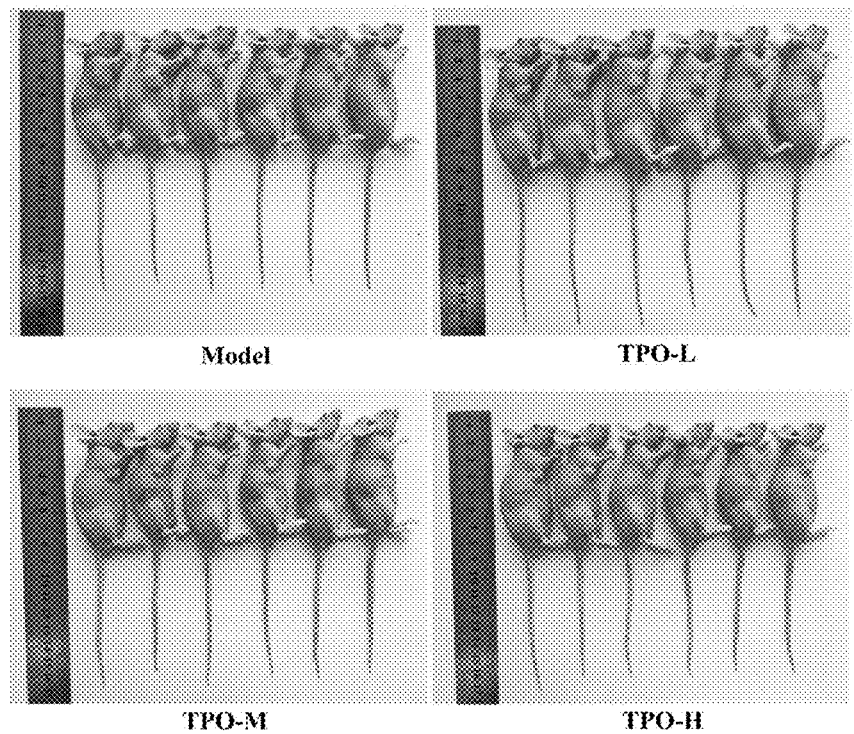
FIG. 5 shows subcutaneous implanted tumors observed on skin surfaces of nude mice.
Figure 6:
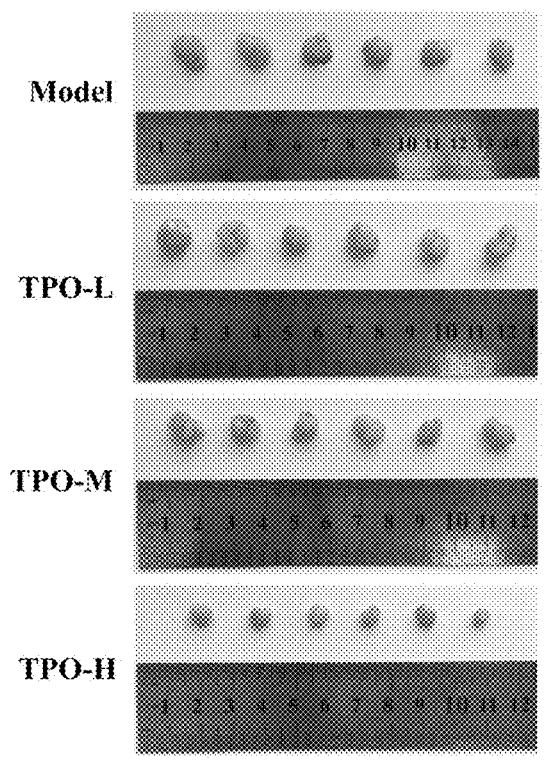
FIG. 6 shows tumor tissues stripped after nude mice are sacrificed.

In the experiment, the nude mice were randomly divided into four groups: a model group (Model), a low-dose group (TPO-L), a middle-dose group (TPO-M) and a high-dose group (TPO-H), the nude mice were sacrificed after continuous administration for 13 days, and implanted tumor tissues and tissue samples were obtained. In the experiment, the growth of the tumor was monitored by the animal in-vivo imaging technology. As shown in FIG. 4, compared with the model group, the fluorescence signals in the tumors of the nude mice in each dose of administration group were significantly weakened and were dose-dependent; and the fluorescence signal in the high-dose group was weakened more obviously, suggesting that the triptolide acrylate (compound shown in formula I) can significantly inhibit the proliferation of liver cancer cells in tumors. As shown in FIG. 5, it can be seen from the subcutaneous implanted tumor and skin surface of the nude mice that the tumor volume of the administration group (especially the high-dose group) was significantly less than that of the model group, and was dose-dependent. Similarly, as shown in FIG. 6, in the tumor tissues stripped after the nude mice were sacrificed, the tumor volume of the administration group was less than that of the model group, thereby further verifying the in-vivo anti-liver cancer effect of the triptolide acrylate.

3.2 In this experiment, the influence of the triptolide acrylate on the expression of important proteins related to apoptosis was also observed.

Figure 7:
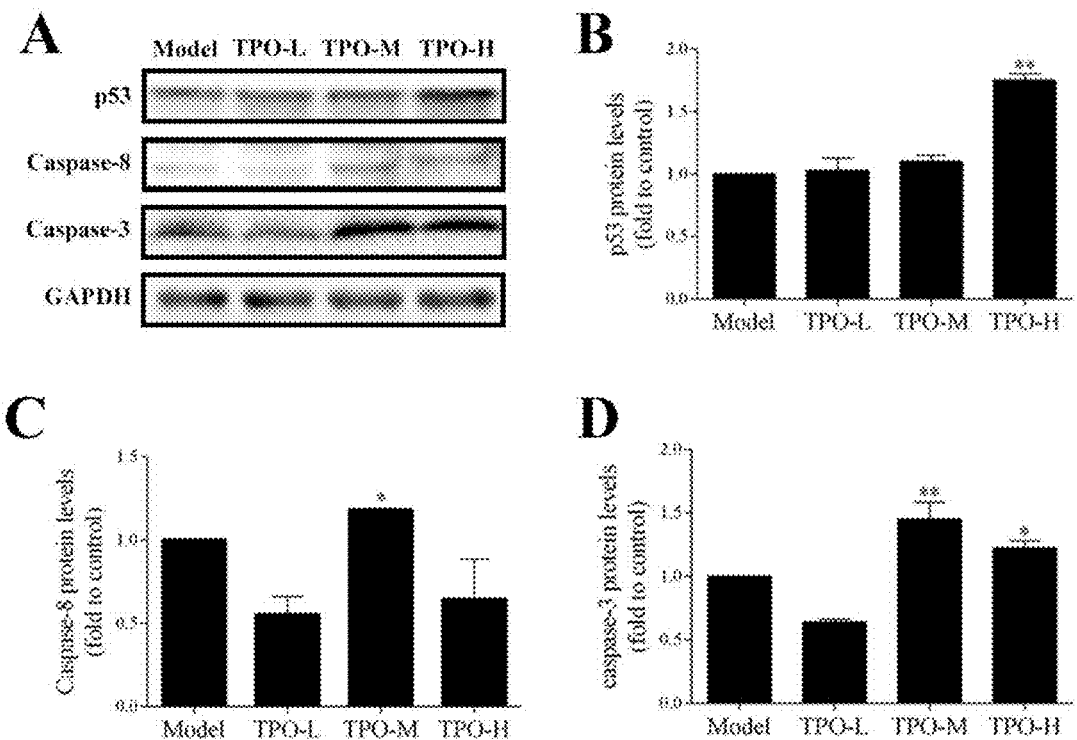
FIG. 7 shows the influence of triptolide acrylate on the expression of important proteins related to apoptosis.

P53 is a very important cancer suppressor gene with multiple biological functions of promoting gene repair, regulating cell cycle progression and inducing cell apoptosis, wherein phosphorylation at serine sites has the effect of promoting cell apoptosis. Caspase-8 and caspase-3 are respectively located at core positions of an initiator and an executor in the caspase cascade reaction, and are the key steps of cell apoptosis and the common pathway of all apoptosis signals. As shown in FIG. 7, the high-dose group can significantly increase the protein expression quantity of p53, while the low-dose group and the middle-dose group have no significant change. The middle-dose group can significantly increase the protein expression quantity of caspase-8, while the low-dose group and the high-dose group can reduce the protein expression quantity of caspase-8. The middle-dose group and the high-dose group can significantly increase the protein expression quantity of caspase-3, while the low-dose group can reduce the protein expression quantity of caspase-3.

II. Effects of Triptolide Acrylate on Proliferation and Apoptosis of Liver Cancer Cells

1. Experimental Materials

1.1 Cell Lines and Drugs

The LO2, HepG2, Hep3B, SMMC-7721 and BEL-7402 cells used in this experiment were purchased from ATCC. The cells were cultured in a DMEM complete medium containing 10% fetal bovine serum, $1\times10^5$ U/L penicillin and 100 mg/L streptomycin at 5% $CO_2$, 37° C. and saturated humidity.

1.2 Reagents

Fetal bovine serum, DMEM medium, penicillin-streptomycin double antibody (Gibco, USA); AnnexinV-FITC/PI apoptosis detection kit, ECL detection kit (Keygen Biotech); MMT kit, BCA protein concentration assay kit, SDS-PAGE protein loading buffer, PMSF, NP40 lysate (Beyotime); β-actin, Caspase-3, cleaved-Caspase-3, PARP, cleaved-PARP antibody and secondary antibody (CST, USA).

1.3 Instruments:
Heal Force biological safety cabinet, NEW Brunswick carbon dioxide incubator, Roche biochemical analyzer, inverted microscope, BD flow cytometer, Bio-rad protein electrophoresis system, BioTek Epoch microplate reader, etc.

2. Experimental Method

2.1 Cell Toxicity Experiment

Logarithmically growing LO2 cells were taken and inoculated in a 96-well plate at $1\times10^4$ cells per well. The cells treated with drugs with final concentrations of 0, 10, 50 and 100 nM were used respectively, the culture supernatant was collected after 24 h, and the LDH activity of the culture supernatant was detected by the Roche biochemical analyzer.

2.2 Detection of Cell Proliferation by MMT Method

When the liver cancer cells grew to the logarithmic phase, the single cell suspension was inoculated in a 96-well plate at $1\times10^4$ cells per well. A blank group was a DMEM medium containing 10% fetal bovine serum, a control group was a solvent-added control (DMSO) cell group, and an experimental group was a cell group treated with drugs with different final concentrations (10, 25, 50, 100 nM). After 24 h of treatment, the medium supernatant was carefully aspirated, and 100 μL of MTT solution with a final concentration of 0.5 mg/L diluted with the medium was added to each well. After the cells were cultured for 4 h, the medium was discarded, 150 μL of DMSO solution was added to each well, and shaking was performed at a low speed on the shaker for 10 min in the dark. After the crystals were fully dissolved, the absorbance (A) of each well was detected at 490 nm with the microplate reader. Cell proliferation inhibition rate=[(control group $A_{450}$–blank group $A_{450}$)–(experimental group $A_{450}$–blank group $A_{450}$)/(control group $A_{450}$–blank group $A_{450}$)]×100%.

2.3 Detection of Cell Apoptosis by Flow Cytometry

Liver cancer cells in the logarithmic growth phase were taken and inoculated in a 12-well plate at $5\times10^5$ cells per well. The cells treated with triptolide acrylate (hereinafter referred to as TPO) and triptolide triol (hereinafter referred to as TP-3-OH) with final concentrations of 0, 50 and 100 nM were used. After 24 h of treatment, the cells were digested and collected with 0.25% EDTA-free pancreatin, washed twice with pre-cooled PBS, and resuspended with 300 μL 1× Binding Buffer. 5 μL FITC Annexin V and 5 μL PI were added to each tube of cell suspension and incubated at a room temperature for 5 min in the dark, and the flow cytometry was used for detection within 1 h.

2.4 Detection of Apoptosis-Related Proteins by Western Blot

BEL-7402 cells in the logarithmic growth phase were taken and inoculated in a 12-well plate at $5\times10^5$ cells per well. The cells treated with TPO with final concentrations of 0, 50 and 100 nM were used. After 24 h of treatment, the cells were collected, then lysate was added, and total proteins were extracted after sufficient lysis on ice. After the protein concentration was measured by a BCA method, the Loading buffer was added and boiled at 100° C. for 10 min to fully denature the proteins. The denatured sample was subjected to SDS-PAGE gel electrophoresis and electrically transferred to a PVDF membrane. The transferred PVDF membrane was sealed with a 5% BSA solution in TBST at a room temperature for 1 h, then incubated overnight with the corresponding primary antibody at 4° C., washed with TBST, incubated with the secondary antibody at a room temperature for 2 h, and washed with TBST again.

Finally, an ECL chemiluminescent solution was added to make the membrane strip emit light, electrophoresis results were obtained by pressing, developing and fixing with photosensitive films, and the change trends of apoptosis-related proteins among different treatment groups were observed.

2.5 Scratch Test

Huh7 cells in the logarithmic growth phase were taken and inoculated in a 24-well plate at $5\times10^5$ cells per well. After the cells were overgrown, a sterile pipette tip was used for scratching, the cells were washed 3 times with PBS after scratching, the scratched cells were removed, a serum-free medium containing 50 nM TPO was added to continue the culture for 24 and 48 h, and photographing was performed. The scratch photo was analyzed by Image J software, the scratch distance was calculated, and the scratch healing was evaluated.

3. Result Treatment and Analysis

3.1 Statistical Analysis

The results were analyzed by SPSS 16.0 software. The statistical data were presented as mean±standard deviation (x̄±s). The data were first tested for normality and homogeneity of variance, the one-way analysis of variance or t-test was used for comparison among groups, and P<0.05 has statistical significance.

Figure 8:
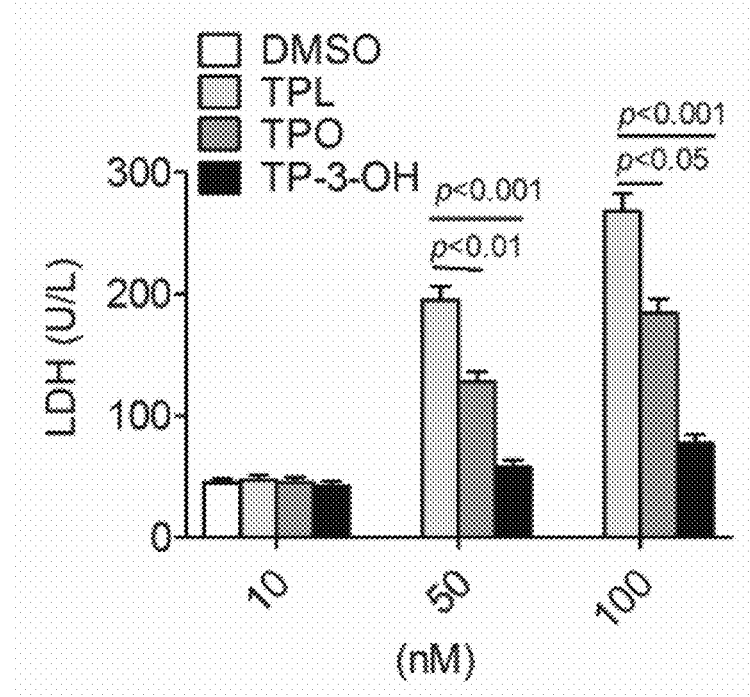
FIG. 8 shows a toxic effect of different concentrations of drugs on LO2 cells.

3.2 Comparison of toxicity of TPL (triptolide), TP-3-OH and TPO on normal liver cells The results of the cell toxicity test in FIG. 8 showed that the LDH activity of the culture supernatant of the LO2 cells treated with TPL was significantly increased, while the LDH activity of the supernatant of the TP-3-OH and TPO treatment groups was significantly lower than that of the TPL treatment group, indicating that the toxicity of TP-3-OH and TPO to liver cells was significantly lower than that of the triptolide.

Figure 9:
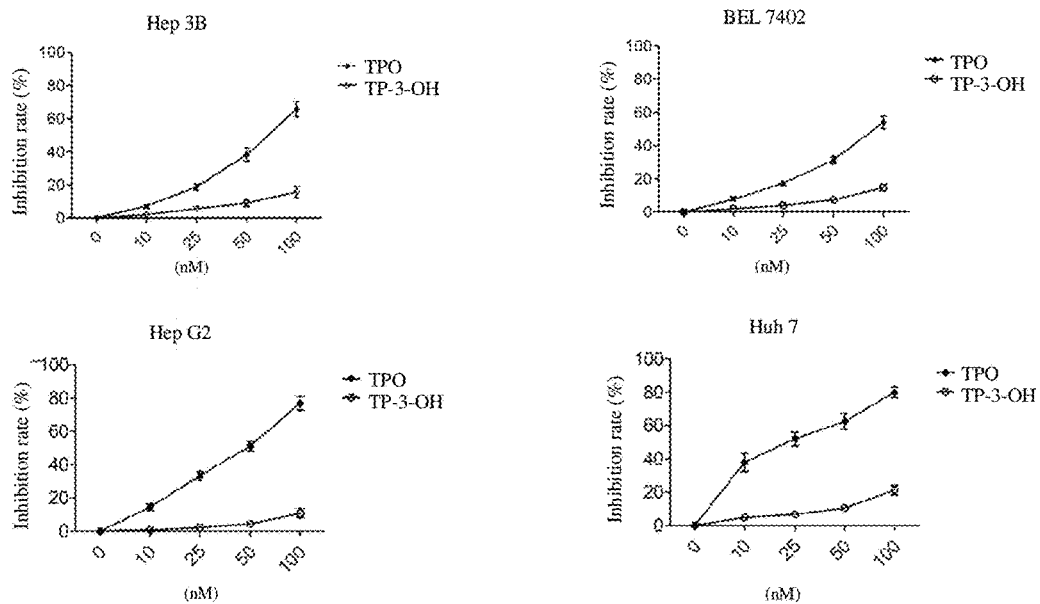
FIG. 9 shows the influence of different concentrations of drugs on a proliferation rate of liver cancer cells.

3.3 Inhibiting Effects of TP-3-OH and TPO on Proliferation of Liver Cancer Cells The MTT experiment results in FIG. 9 showed that TPO has a significant inhibiting effect on proliferation of HepG2, Hep3B, SMMC-7721 and BEL-7402 liver cancer cells, and the effect is dose-dependent, indicating that TPO has an inhibiting effect on proliferation of liver cancer cells. TP-3-OH has no obvious inhibiting effect on proliferation of liver cancer cells.

3.4 Induction Effect of TPO on Apoptosis of Liver Cancer Cells

Figure 10:
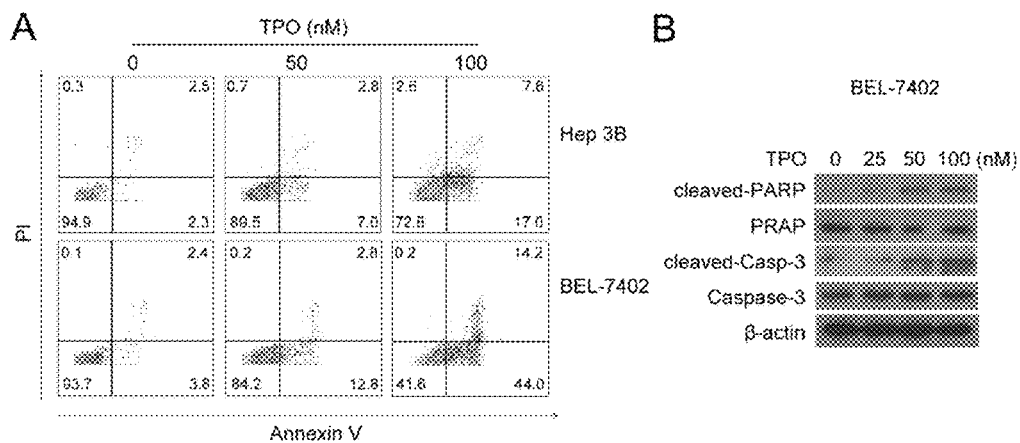
FIG. 10 shows an induction effect of different concentrations of triptolide acrylate on the apoptosis of liver cancer cells.

The flow cytometry results in FIG. 10 showed that the proportion of Annexin V and PI positive cells in Hep3B and BEL-7402 liver cancer cells was significantly increased after TPO treatment (A). The western blot results in FIG. 10 showed that the cleavage of Caspase-3 and PARP in BEL-7402 cells was significantly increased after TPO treatment (B), indicating that TPO has the effect of inducing apoptosis of liver cancer cells. The induction effect of TP-3-OH on apoptosis of liver cancer cells was not obvious (results were not shown).

3.5 Inhibiting Effect of TPO on Metastasis of Liver Cancer Cells

Figure 11:
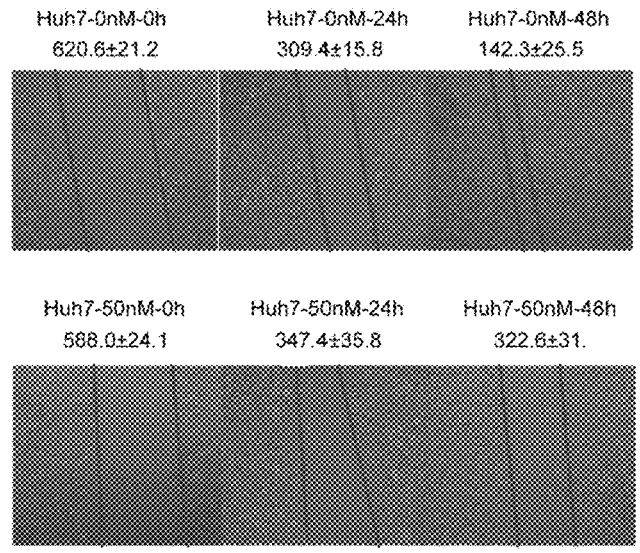
FIG. 11 shows an inhibiting effect of triptolide acrylate on metastasis of liver cancer cells.

The scratch test results in FIG. 11 showed that TPO can significantly inhibit the migration of Huh7 cells, and the difference has statistical significance (P<0.05), suggesting that TPO may have the effect of inhibiting metastasis of liver cancer cells.

The foregoing are merely some of the examples of the present invention. Without departing from the concept of the present invention, those skilled in the art can also make several modifications and improvements, and these modifications and improvements all fall within the protection range of the present invention.

What is claimed is:

1. A Triptolide acrylate, wherein the triptolide acrylate is a compound shown in formula (I) or a pharmaceutically acceptable salt thereof.

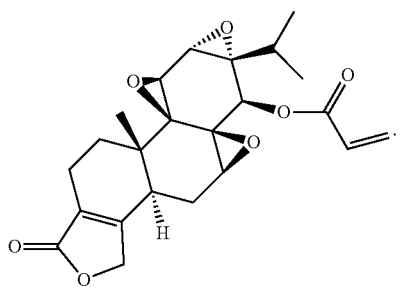

(I)

2. The preparation method for the triptolide acrylate according to claim 1, comprising the following steps:
   (1) adding triptolide and an acylating reagent to an organic solvent, using 4-dimethylaminopyridine as a catalyst and triethylamine as an acid binding agent, performing stirring at a room temperature for 1-4 h, and quenching the reaction with a saturated aqueous sodium bicarbonate solution; and
   (2) performing extraction with dichloromethane, washing the extract with a saturated aqueous sodium chloride solution, then performing drying with a desiccant, performing evaporation to dryness under reduced pressure, and performing purification by silica gel column chromatography, thereby obtaining a compound of Formula (I).

3. The preparation method for the triptolide acrylate according to claim 2, wherein step (1) may comprise:
   dissolving triptolide and 4-dimethylaminopyridine in an organic solvent, adding triethylamine, performing ice bath to about 0° C., dropwise adding an acylating reagent, returning the temperature to a room temperature after dropwise adding, performing stirring for 1-4 h, performing TLC to detect whether the reaction is complete, stopping stirring, and quenching the reaction with a saturated aqueous sodium bicarbonate solution.

4. The preparation method for the triptolide acrylate according to claim 2, wherein step (2) may comprise:
   performing extraction with dichloromethane, extracting an aqueous layer with dichloromethane twice, mixing the dichloromethane extracts obtained in three times, washing the mixed extract with a saturated aqueous sodium chloride solution, then performing drying with a desiccant, performing evaporation to dryness under reduced pressure, and performing purification by silica gel column chromatography to obtain the triptolide acrylate.

5. The preparation method for the triptolide acrylate according to claim 2, wherein the acylating reagent is one or more of acryloyl chloride, acryloyl bromide, acrylic anhydride and acrylic acid.

6. The preparation method for the triptolide acrylate according to claim 5, wherein the organic solvent is anhydrous dichloromethane, trichloromethane, tetrahydrofuran or diethyl ether.

7. The preparation method for the triptolide acrylate according to claim 6, wherein the desiccant is one or more of anhydrous sodium sulfate, anhydrous magnesium sulfate and anhydrous calcium chloride.

* * * * *